United States Patent [19]

Ecker et al.

[11] 4,328,213

[45] May 4, 1982

[54] STABLE INJECTABLE LABETALOL FORMULATION

[75] Inventors: Varda Ecker, New York, N.Y.; Yogendra M. Shah, Piscataway; Imtiaz A. Chaudry, Denville, both of N.J.

[73] Assignee: Schering Corporation, Kenilworth, N.J.

[21] Appl. No.: 98,166

[22] Filed: Nov. 28, 1979

[51] Int. Cl.³ .................. A61K 47/00; A61K 31/165; A61K 31/615; A61K 31/36
[52] U.S. Cl. ................................. 424/173; 424/176; 424/180; 424/233; 424/282; 424/319; 424/324
[58] Field of Search ............... 424/173, 176, 180, 230, 424/233, 282, 319, 324

[56] References Cited

U.S. PATENT DOCUMENTS

| | | | |
|---|---|---|---|
| 3,644,469 | 2/1972 | Koppe | 424/282 |
| 4,163,053 | 7/1979 | Neustadt | 424/230 |

FOREIGN PATENT DOCUMENTS

| | | |
|---|---|---|
| 2867 | 7/1979 | European Pat. Off. . |
| 1541933 | 3/1979 | United Kingdom . |

OTHER PUBLICATIONS

Clinical Trials Journal, 1977 vol. 14, No. 2, pp. 80-81 (Phillips).

*Primary Examiner*—Anna P. Fagelson
*Attorney, Agent, or Firm*—Warrick E. Lee, Jr.; Vincent H. Gifford; Bruce M. Eisen

[57] ABSTRACT

An injectable formulation for the pharmaceutically acceptable acid addition salts of labetalol, its isomers and mixtures thereof is provided which has enhanced stability properties.

10 Claims, No Drawings

STABLE INJECTABLE LABETALOL FORMULATION

BACKGROUND OF THE INVENTION

The pharmaceutically acceptable acid addition salts of Labetalol and its isomers and mixtures thereof are useful cardiovascular drugs used, for instance, in the treatment of hypertension and cardiac arrhythmias. See, for instance, U.S. Pat. No. 4,012,444, British Pat. Nos. 1,541,932 and 1,541,933, and U.S. Ser. No. 089,077, filed Oct. 29, 1979, of common assignee as the instant application. Labetalol hydrochloride is marketed, e.g., in Great Britain, in an injectable formulation under the trade name Trandate ®. The formulation marketed consists of 5.0 mg/ml labetalol hydrochloride, 8.1 mg/ml sodium chloride and sterile water for injection. This formulation has been found to be unsuitable for long-term shelf life due to the formation of particulate matter when stored for 3 months at temperatures of 45°–55° C. or at refrigerator temperature (5°–6° C.)

SUMMARY OF THE INVENTION

The present invention is concerned with a stable injectable formulation of a pharmaceutically acceptable acid addition salt of labetalol, its isomers or mixtures thereof. More particularly, this invention relates to a stable injectable formulation comprising, per ml of solution:

- 3–5 mg pharmaceutically acceptable acid addition salt of labetalol or any of its four isomers or mixtures thereof;
- 10–60 mg non-ionic isotonic agent;
- 0.1–2.0 mg paraben preservative or mixtures thereof;
- sufficient organic acid to obtain a pH of 3.0–4.0;
- water for injection q.s. 1.0 ml.

DESCRIPTION OF THE INVENTION

According to the present invention, it has now been found that a stable injectable formulation of a pharmaceutically acceptable acid addition salt of labetalol, its isomers or mixtures thereof, can be attained by utilization of particular ingredients in particular proportions.

A non-ionic isotonic agent is utilized to adjust the tonicity of the solution to that of the human blood. Such agents suitable are dextrose and glycine, with dextrose being highly preferred. The exact amount utilized per ml of formulation is dependent upon the amount of the pharmaceutically acceptable acid addition salt of labetalol or isomer or mixtures thereof; the amount of paraben preservatives, the amount of organic acid, and the amount of optional ingredients. Most preferably, however, the amount utilized is 40–50 mg/ml of final formulation.

The paraben preservative utilized may be any of the esters of parahydroxybenzoic acid, or mixtures thereof commonly utilized for injectable pharmaceutical formulations, e.g., methyl paraben, ethyl paraben, propyl paraben and butyl paraben. Of these, methyl paraben and propyl paraben and mixtures thereof are highly preferred. The paraben preservative is present in the formulation in a concentration of 0.1–2.0 mg/ml of final formulation. A particularly preferred concentration of the paraben preservatives is that wherein about 0.8 mg methyl paraben and about 0.1 mg propyl paraben is present in 1.0 ml of the final formulation. Since the parabens act synergistically, a smaller total amount of paraben preservative is necessary when a mixture of parabens is utilized. A single paraben preservative, e.g., methyl paraben, would preferably be utilized at a higher concentration, e.g., 1.5 mg/ml final formulation.

The organic acid utilized for pH adjustment is added in a quantity sufficient to adjust the pH to 3.0 to 2.0 The exact amount is necessarily dependent on the particular organic acid utilized, but generally is in the range of 0.05 to 1.0 mg/ml and for citric acid in the range of about 0.05 to about 0.9 mg/ml. Suitable organic acids are those such as citric, succinic or tartaric with citric acid being most highly preferred. In a most highly preferred embodiment of this invention the final pH is adjusted to about 3.5±0.2.

Optionally, up to about 0.2 mg/ml of a metal chelating agent may be added to the formulation to further enhance the stability of the pharmaceutically acceptable acid addition salt of labetalol, its isomers or mixtures thereof. A particularly useful agent for this purpose is edetate disodium.

The pharmaceutically acceptable acid addition salt of labetalol, its isomers or mixtures thereof utilized in the present invention may be any such salt derived from common acids utilized for this purpose. Preferred salts are the sulfate, maleate, tartrate, citrate and the hydrochloride, with the hydrochloride being most particularly preferred.

The following examples describe in detail the formulations of the present invention. It will be apparent to those skilled in the art that many modifications, both of materials and methods, may be practiced without departing from the spirit and scope of the invention.

EXAMPLE 1

| Ingredient | mg/ml |
| --- | --- |
| Labetalol hydrochloride | 5.00 |
| Dextrose | 45.00 |
| Methyl Paraben | 0.80 |
| Propyl Paraben | 0.10 |
| Edetate Disodium | 0.10 |
| Citric Acid Monohydrate | 0.11 |
| Water for injection    q.s. ad. | 1.00 ml |

Procedure for formulation:

Dissolve the methyl and propyl parabens in a portion of water for injection at 60°–70° C., and cool the solution to 25°–35° C. Charge and dissolve all other excipients and the active ingredient. Bring the solution to final volume, filter it through a sterilizing membrane and fill into sterile containers.

EXAMPLE 2

| Ingredient | mg/ml |
| --- | --- |
| Labetalol hydrochloride | 5.00 |
| Dextrose | 45.00 |
| Methyl Paraben | 1.30 |
| Propyl Paraben | 0.20 |
| Edetate Disodium | 0.10 |
| Citric Acid Monohydrate | 0.086 |
| Water for injection    q.s. ad. | 1.00 ml |

Procedure for formulation:

Dissolve the methyl and propyl parabens in a portion of water for injection at 60°–70° C., and cool the solution to 25°–35° C. Charge and dissolve all other excipients and the active ingredient. Bring the solution to final volume, filter it through a sterilizing membrane and fill into sterile containers.

EXAMPLE 3

| Ingredient | mg/ml |
|---|---|
| Labetalol hydrochloride | 5.00 |
| Glycine | 20.00 |
| Methyl Paraben | 0.80 |
| Propyl Paraben | 0.10 |
| Edetate Disodium | 0.10 |
| Citric Acid Monohydrate | 0.11 |
| Water for injection     q.s. ad. | 1.00 ml |

Procedure for formulation:

Dissolve the methyl and propyl parabens in a portion of water for injection at 60°-70° C., and cool the solution to 25°-35° C. Change and dissolve all other excipients and the active ingredient. Bring the solution to final volume, filter it through a sterilizing membrane and fill into sterile containers.

EXAMPLE 4

| Ingredient | mg/ml |
|---|---|
| R,R-enantiomer hydrochloride of labetalol | 5.00 |
| Dextrose | 45.00 |
| Methyl Paraben | 0.80 |
| Propyl Paraben | 0.10 |
| Edetate Disodium | 0.10 |
| Citric Acid Monohydrate | 0.12 |
| Water for injection     q.s. ad. | 1.00 ml |

Procedure for formulation:

Dissolve the methyl and propyl parabens in a portion of water for injection at 60°-70° C., and cool the solution to 25°-35° C. Change and dissolve all other excipients and the active ingredient. Bring the solution to final volume, filter it through a sterilizing membrane and fill into sterile containers.

What is claimed is:

1. A stable injectable pharmaceutical formulation which comprises, per ml of solution
   3-5 mg pharmaceutically acceptable acid addition salt of labetalol, or any of its four isomers or mixtures thereof;
   10-60 mg non-ionic isotonic agent;
   0.1-2.0 mg paraben preservative or mixtures thereof;
   sufficient organic acid to obtain a pH of 3.0-4.0;
   water for injection q.s. 1.0 ml.

2. A formulation according to claim 1 wherein the pharmaceutically acceptable acid addition salt is the hydrochloride salt.

3. A formulation according to claim 1 wherein the non-ionic isotonic agent is dextrose.

4. A formulation according to claim 2 wherein the non-ionic isotonic agent is glycine.

5. A formulation according to claim 2 wherein the organic acid is citric acid.

6. A formulation according to claim 2 wherein the paraben preservative is a mixture of methyl paraben and propyl paraben.

7. A formulation according to claim 2 wherein the pH is 3.5±0.2.

8. A formulation according to claim 2 which additionally includes disodiuum edetate in an amount of 0.1 mg/ml.

9. A formulation according to claim 2 which, per ml, is:
   3-5 mg labetalol hydrochloride;
   45.00 mg dextrose;
   0.80 mg methyl paraben;
   0.10 mg propyl paraben;
   0.10 mg edetate disodium;
   0.11 mg citric acid monohydrate; and
   water for injection q.s. 1.0 ml.

10. A formulation according to claim 2 which, per ml, is:
   5.00 mg R,R-enantiomer hydrochloride of labetalol;
   45.00 mg dextrose;
   0.80 mg methyl paraben;
   0.10 mg propyl paraben
   0.10 mg edetate disodium;
   0.12 mg citric acid monohydrate; and
   water for injection q.s. 1.00 ml.

* * * * *